United States Patent [19]

Shoesmith

[11] Plant 4,468

[45] Oct. 23, 1979

[54] CHRYSANTHEMUM NAMED BOUNTY

[75] Inventor: Leonard H. Shoesmith, Westfield-Woking, England

[73] Assignee: Pan-American Plant Company, West Chicago, Ill.

[21] Appl. No.: 955,002

[22] Filed: Oct. 26, 1978

[51] Int. Cl.[2] ..... A01H 5/00

[52] U.S. Cl. ..... Plt./77

[58] Field of Search ..... Plt./77

*Primary Examiner*—Robert E. Bagwill

*Attorney, Agent, or Firm*—Chas. W. Rummler

[57] ABSTRACT

A new variety of chrysanthemum plant intended for glass house culture for cut flower production distinguished by its creamy white incurved blooms of excellent form and medium size, and by its resistance to sunscald and botrytis.

4 Drawing Figures

BACKGROUND OF THE NEW PLANT

This chrysanthemum cultivar originated as a seedling of unknown parentage growing in a field of chrysanthemums maintained by me at Westfield-Woking, Surrey, England, for breeding purposes. The new plant was discovered by me in 1973 and the fine form of the bloom with its creamy white and light yellow coloration led me to propagate this plant for test purposes. Propagation was done by me and under my direction at Westfield-Woking by means of cuttings from the original plant with satisfactory results and further propagation through successive generations, with vegetative cuttings, has shown this variety to retain its distinctive characteristics from generation to generation and these novel characteristics appear to be firmly fixed.

This new chrysanthemum cultivar is now being propagated on a commercial scale by means of vegetative cuttings at West Chicago, Ill., and at Cortez, Fla.

DESCRIPTION OF THE DRAWINGS

My new chrysanthemum plant is illustrated by the accompanying drawings, the first of which is a full color photographic rendition showing the form and coloration of the blossoms of the plant, as reproduced by conventional photographic procedures. The second drawing is a machine reproduction of a photocopy of typical leaves of the new plant showing their distinctive form.

DESCRIPTION OF THE NEW PLANT

The following is a detailed description of my new chrysanthemum variety with color specifications according to the R.H.S. Colour Chart published by The Royal Horticultural Society of London, England, in collaboration with The British Colour Council, these observations having been made in the summer of 1978 of plants grown in greenhouse at West Chicago, Ill., U.S.A.

THE PLANT

Origin: Seedling.

Parentage: Unknown, this seedling having been a selection from plants resulting from random crosses.

Classification:

*Botanic.*—*Chrysanthemum morifolium.*

*Commercial.*—Greenhouse Cut Flower Plant.

Form: Perennial herbaceous bush.

Height: 105 to 121 cm.

Growth: Upright and terminal, sturdy and vigorous with very good strength.

Branching: Under normal conditions.

Foliage: Abundant in quantity, producing about 4 to 5 leaves on about 15 cm. of stem.

*Leaf size.*—8.7 to 15.8 cm. long and 5.1 to 9.9 cm. wide.

*Shape.*—Lobed, lanceolate and slightly serrated.

*Surface aspect.*—Canescent.

*Venation.*—Pinnate.

*Color.*—Upper side — 147A. Under side — 147B.

*Petioles.*—About 1.6 to 3.9 cm. long.

THE BUD

Form: Elliptical.

Size: About 15 to 17 mm. in diameter and about 9 to 11 mm. in depth.

Opening rate: Bud opens slowly.

Color:

*When phyllaries first divide.*—4C.

*When florets begin to unfurl.*—2D.

Phyllaries: The receptacle bears many involucral spear-shaped upstanding bracts on its outside.

*Color.*—Inside — 137A. Outside — 137B.

*Surface aspect.*—Pubescent.

Peduncle: Length — about 2.5 to 4.0 cm.

*Surface texture.*—Pubescent.

*Strength.*—Erect and very strong.

THE FLOWER

Recommended flowering: Year around with photoperiod control.

Response: 9 week.

Natural flowering season: October 27 to November 5.

Blooms: Flower type: Composite and incurved.

*Borne.*—As a head of many florets on a single receptacle.

*Size.*—Medium, about 11 to 14 cm. in diameter and about 9 to 12 cm. in depth.

*Shape.*—Cup-shaped with high center when bloom first opens, becoming globular as the bloom matures.

Florets: Numerous in quantity.

*Form.*—Incurved spoon with obtuse apex.

*Color.*—Outer florets: Upper side — 155D. Reverse side — 155D. Inside florets: Upper side — 4D. Reverse side — 4D.

*Firmness.*—Medium.
*Appearance.*—Very slight shine.
*Discoloration after full bloom.*—None.
Peduncle: Sturdy and upright.
*Length.*—About 2.5 to 4.0 cm.
*Color.*—147B.
Persistence: Florets hang on and dry.
Effect of weather: Recommended for greenhouse culture only.
Fragrance: Typical chrysanthemum.
Lasting quality:
*On plant.*—3 to 4 weeks.
*As cut flower.*—10 to 17 days.

REPRODUCTIVE ORGANS

Stamens: Arrangement — syngenesius.
*Number.*—5, with anthers.
*Filaments.*—About 2 to 4 mm. long. Color: Light yellow.
*Pollen.*—Color — yellow.

Pistils: Number — One to each ray and disc floret.
*Styles.*—About 4 to 6 mm. long.
*Stigmas.*—Color — yellow.
*Ovaries.*—Inferior bicarpellate.

This cultivar of chrysanthemum is particularly characterized by the creamy white incurved blooms which exhibit excellent form retention and measuring about 11 to 14 cm. in diameter when grown as a disbudded standard. This plant has a uniform, year around, 9 week photoperiodic response; is resistant to sunscald and botrytis; and has durable dark green and glossy foliage.

I claim:

1. A new and distinct cultivar of chrysanthemum plant, substantially as herein shown and described, characterized by its capability of year around production of medium sized flowers having a creamy white and light yellow coloration when grown under glass with photoperiodic control.

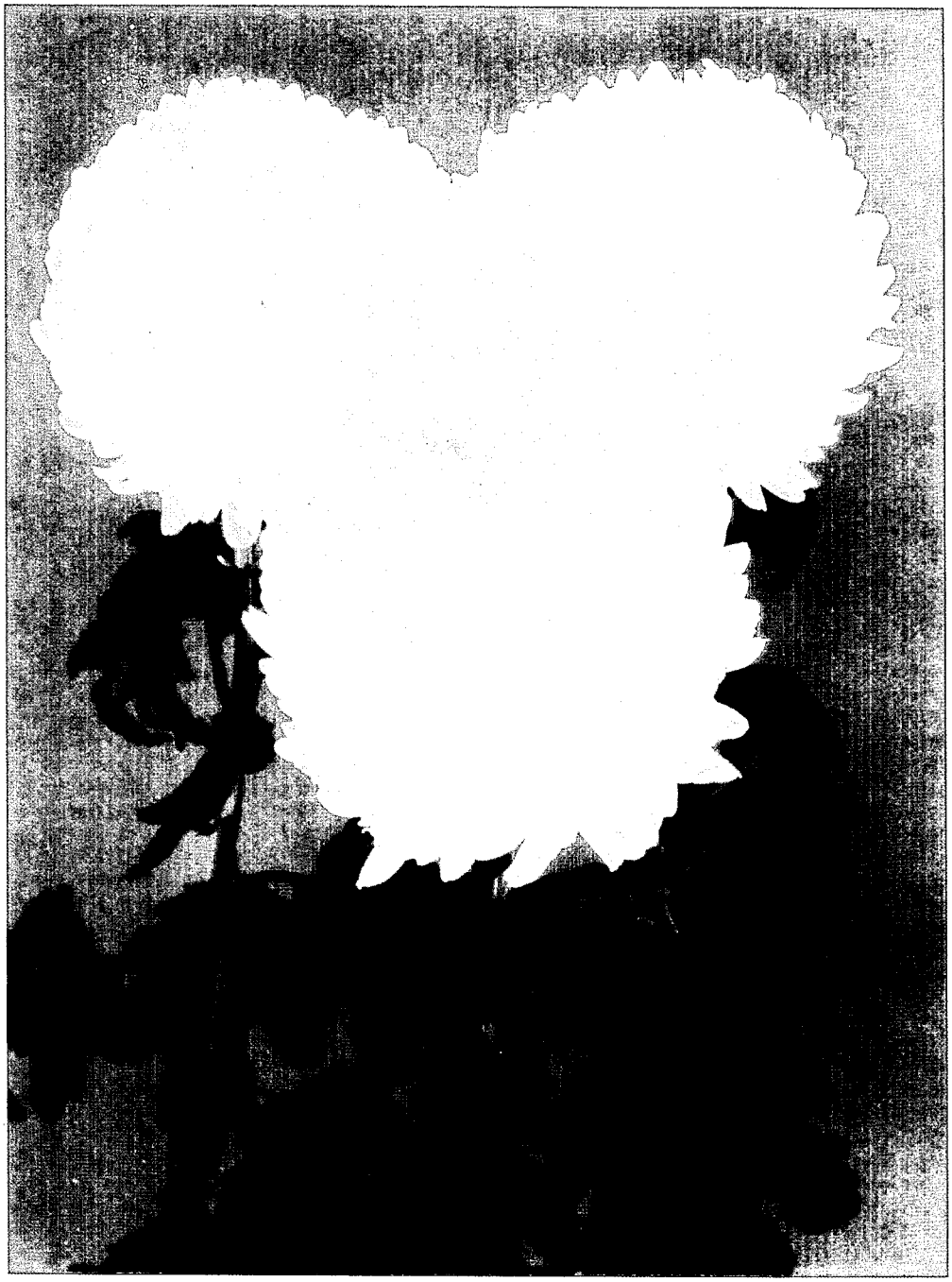

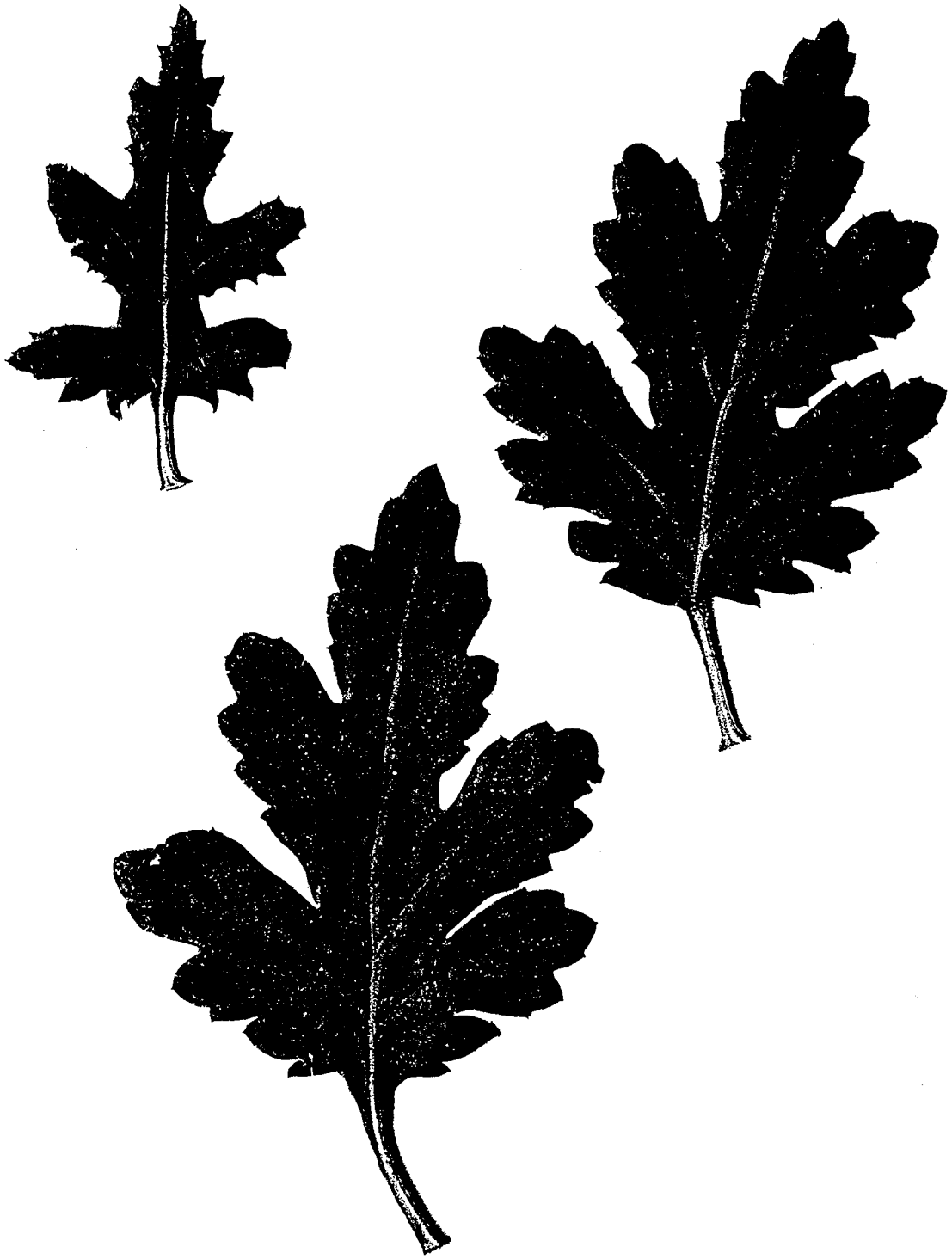

* * * * *